United States Patent
Mori et al.

(10) Patent No.: US 8,173,109 B2
(45) Date of Patent: May 8, 2012

(54) EYELASH COSMETIC

(75) Inventors: Atsumi Mori, Yokohama (JP); Hideki Takahashi, Yokohama (JP); Satoshi Tomomasa, Yokohama (JP); Hiroyuki Yokoyama, Yokohama (JP)

(73) Assignee: Shiseido Co., Ltd., Chou-ku, Tokyo (JP)

( * ) Notice: Subject to any disclaimer, the term of this patent is extended or adjusted under 35 U.S.C. 154(b) by 0 days.

(21) Appl. No.: 12/577,263

(22) Filed: Oct. 12, 2009

(65) Prior Publication Data

US 2010/0028283 A1      Feb. 4, 2010

Related U.S. Application Data

(63) Continuation of application No. 10/550,937, filed as application No. PCT/JP2004/004628 on Mar. 31, 2004, now abandoned.

(30) Foreign Application Priority Data

Mar. 31, 2003   (JP) .................... 2003-96658

(51) Int. Cl.
*A61K 8/00* (2006.01)
*A61K 8/18* (2006.01)
*A61Q 1/02* (2006.01)
*A61Q 19/04* (2006.01)
*A61K 9/00* (2006.01)
*A61K 8/02* (2006.01)

(52) U.S. Cl. ............................ 424/63; 424/400; 424/401
(58) Field of Classification Search .................. 424/400, 424/401, 63
See application file for complete search history.

(56) References Cited

U.S. PATENT DOCUMENTS

| | | |
|---|---|---|
| 5,612,021 A | 3/1997 | Mellul |
| 5,637,291 A | 6/1997 | Bara et al. |
| 5,876,704 A | 3/1999 | Collin et al. |
| 6,264,933 B1 * | 7/2001 | Bodelin et al. ............... 424/70.7 |

FOREIGN PATENT DOCUMENTS

| | | |
|---|---|---|
| JP | 11060440 A * | 3/1999 |
| KR | 10-0250177 | 5/2000 |

OTHER PUBLICATIONS

Machine translation of JP/11/060440.*
3M Scotchlite Glass Bubbles technical brief, Mar. 2002, (retrieved on Aug. 26, 2008), retrieved from www.rtpcompany.com, five pages.
Expancel product identification sheet (retrieved Aug. 26, 2008), retrieved from www.expancel.com, one page.
International Search Report for PCT/JP2004/004628 mailed Jul. 6, 2004, two pages.
Japanese Patent Abstract for Publication No. 08-012528 published Jan. 16, 1996, three pages.
Japanese Patent Abstract for Publication No. 11-049642 published Feb. 23, 1999, two pages.
Japanese Patent Abstract for Publication No. 11-060440 published Mar. 2, 1999, one page.
Supplementary European Search Report for EP 04724751 mailed Jul. 3, 2006, three pages.

* cited by examiner

*Primary Examiner* — Johann Richter
*Assistant Examiner* — Luke Karpinski
(74) *Attorney, Agent, or Firm* — Rankin, Hill & Clark LLP

(57) ABSTRACT

An eyelash cosmetic according to present invention, by blending (a) wax and/or (b) resin, and (c) hollow powder, can impart a voluminous feeling and, at the same time, perform excellent curling effect and curl retaining effect, and excellent usability such as easiness eyelash coating, and easiness overlaying, and also perform excellent uniformity of finishing, water resistance and oil resistance after coating.

20 Claims, No Drawings

EYELASH COSMETIC

RELATED APPLICATIONS

This application claims priority to the Japanese Patent Application 2003-096658 dated on Mar. 31, 2003 is hereby incorporated with reference for all purposes.

BACKGROUND OF THE INVENTION

1. Field of the Invention

The present invention relates to an eyelash cosmetic. More particularly, the present invention relates to an eyelash cosmetic imparting a voluminous feeling, which has never been seen before and, at the same time, having an excellent curling effect and curl retaining effect.

2. Prior Art

An eyelash cosmetic, a representative of which is mascara, is required to have the effect of making an eyelash concentrated and long, and of imparting voluminous feeling to an eyelash. In addition, it is required the effect of the function such as cosmetic retention (water resistance, sebum resistance), a curling effect (an effect of rapid drying property and of curling and turning upward an eyelash), and a curl retaining effect (an effect of retaining curl with time). In recent years, demand on improvement in a voluminous feeling of an eyelash has been particularly increased.

In general, these eyelash cosmetics are constructed of a solid oil ingredient such as a wax, and a powder, and a film-forming agent as a main component. In order to realize comfortable usability, a feeling of use and function as a cosmetic, blending of a wax, a powder and a film-forming agent having various properties and natures is being studied. For example, by increasing an amount of a wax, a powder and a thickener to be blended, a solid part remaining on an eyelash is increased, and a volume effect of making an eyelash thick and striking is realized. And by using a film agent, which forms a firm film on an eyelash, a curling effect is given, making expression of eyes clear.

However, hitherto, when one tries to enhance a volume effect, a solid part of mascara is increased, a heavy film eliminates curl of an eyelash, and it is difficult to enhance a curling effect, particularly, a curl retaining effect. In addition, when one tries to lighten a film in order to enhance a curling effect or a curl retaining effect, an amount of a solid part remaining on an eyelash can not be increased, and it is difficult to enhance a volume effect. That is, it was established that it is difficult to realize a volume effect and a curling effect or a curl retaining effect simultaneously because these are mutually exclusive events.

On the other hand, hitherto, as a cosmetic in which a hollow expanded resin powder prepared by a method of heating and expanding a thermoplastic resin powder with a volatile expanding agent encapsulated therein is blended, foundation has been studied (e.g. Japanese Patent Application Laid-Open (JP-A) No. 11-60440)).

SUMMARY OF THE INVENTION

The present invention was performed in view of the aforementioned circumstances, and an object of the present invention is to provide an eyelash cosmetic imparting a voluminous feeling, which has never been seen before and, at the same tine, having an excellent curling effect and curl retaining effect, having excellent usability such as easy eyelash coating, and easy overlaying, and also having excellent uniformity of finishing, water resistance and oil resistance after coating.

In order to attain the aforementioned object, the present inventors intensively studied, as a result, found out that, by blending a wax and/or a resin, and a hollow powder together, a volume effect is excellent, finishing is not deteriorated and, at the same time, a curling effect and a curl retaining effect can be improved, which resulted in completion of the present invention.

That is, the present invention relates to an eyelash cosmetic comprising; (a) a wax and/or (b) a resin, and (c) a hollow powder. In addition, it is preferable that the eyelash cosmetic of the present invention comprising; 0.1 to 55% by mass of (a) a wax and/or (b) a resin, and 0.01 to 20% by mass of (c) a hollow powder. In addition, in the eyelash cosmetic of the present invention, it is preferable that a ratio of cubic volume of (a) a wax and/or (b) a resin to cubic volume of (c) a hollow powder is 1:10 to 1:0.01. In addition, it is preferable that the eyelash cosmetic of the present invention comprising; 1 to 30% by mass of (a) a wax, 0.1 to 25% by mass of (b) a resin, and 0.01 to 20% by mass of (c) a hollow powder. In addition, it is preferable that the eyelash cosmetic of the present invention further comprising 0.1 to 30% by mass of (d) a coloring material. In addition, it is preferable that the eyelash cosmetic of the present invention further comprising 0.1 to 20% by mass of (e) a thickener. In addition, in the eyelash cosmetic of the present invention, it is preferable that a specific gravity of a composition after solvent volatilization is 0.1 to 1.0. In addition, in the eyelash cosmetic of the present invention, it is preferable that a hardness at 30° C. (card meter; 8 mmφ/200 g load value) is in a range of 70 to 180.

DESCRIPTION OF THE PREFERRED EMBODIMENT

The (a) wax used in the present invention means an oily ingredient which is solid at a normal temperature, is not particularly limited as far as it is such the oily ingredient. Examples include beeswax, candelilla wax, cotton wax, carnauba wax, bayberry wax, insect wax, whale wax, montan wax, bran wax, lanolin, kapok wax, Japan wax, lanolin acetate, liquid lanolin, sugar cone wax, lanolin fatty acid isopropyl, hexyl laurate, cyclic lanolin, jojoba wax, hard lanolin, shellac wax, beeswax, microcrystalline wax, paraffin wax, POE lanolin alcohol ether, POE lanolin alcohol acetate, POE cholesterol ether, lanolin fatty acid polyethylene glycol, fatty acid glyceride, hardened castor oil, vaseline, POE hydrogenated lanolin alcohol ether, silicone wax, and jojoba ester. These waxes are used by selecting one or more kinds. Among them, microcrystalline wax and candelilla wax are particularly preferable.

The (b) resin used in the present invention is a compound which functions as a film-forming agent, and is not particularly limited as far as it is a resin, which is usually blended in a cosmetic as a film-forming agent. Examples include a fluorine resin, a silicone resin, an aromatic hydrocarbon resin, a terpene resin, polybutene, polyisoprene, an alkyd resin, a PVP-modified polymer, a polyvinylpyrrolidone-modified polymer, a polymer emulsion resin, polyvinyl alcohol, polyvinylpyrrolidone, polyvinyl acetate, polyalkyl acrylate, a rosin acid-based resin, a candelilla resin, polyurethane, a cellulose derivative such as alkylcellulose and nitrocellulose, and dextrin. Examples of the fluorine resin include a resin in which a hydrocarbon main chain has a perfluoroalkyl group in a pendant manner, such as a perfluoroalkyl group-containing acryl resin, and a perfluoroallkyl group-containing methacryl resin; a resin in which a main chain itself is fluorocarbon such as polyvinylidene fluoride; a resin in which a main chain has both of a hydrocarbon part and a fluorocarbon part, obtained by radical copolymerization of fluoroethylene and hydrocarbon-based vinyl ether, being not limiting to the aforementioned compounds. Examples of a commercially available product in a form in which this fluorine resin is dissolved in a volatile oil include Fluorocoat EC-104, EC-106, EC-200, and EC-300 (all manufactured by Asahi Glass Co., Ltd.). As a silicone resin, a copolymer composed of a structural unit of $SiO_2$, $RSiO_{3/2}$, or $R_2SiO$ (R is hydrogen, a hydrocarbon group of a carbon number of 1 to 6, or a phenyl group), or a copolymer in which a terminal thereof is sealed with $R_3SiO_{1/2}$ (R is as defined above) can be used. Examples of a commercially available product include KF7312J, X-21-5249, X-21-5250, and KF9021 (manufactured by Shin-Etsu Chemical Co., Ltd.), and BY11-018 (manufactured by Toray Dow Corning Silicone Corporation). Alternatively, an acryl-silicone-based graft polymer obtained by radical-polymerizing a dimethylpolysiloxane compound having a radical polymerizable group on one end of a molecular chain and a radical polymerizable monomer containing acrylate and/or methacrylate as a main component, a silicone rubber in which a polymerization degree (n) of dimethylpolysiloxane is 5,000 to 8,000, trimethylsiloxysilylpropylcarbamic acid and a fluorine-modified silicone resin may also be used. In addition, Nisseki Neo Polymer T, Neo Polymer 120, Neo Polymer 140 (all manufactured by NIPPON PETROCHEMICALS COMPANY, LTD.) as an aromatic hydrocarbon resin; Quintone A-100, Quintone B-170, Quintone C-100 (all manufactured by NIPPON ZEON CORPORATION) as a terpene-based resin; polybutene 200 (manufactured by Idemitsu Kousan Co., Ltd.) as a polybutene; Escoltz 1071, Escoltz 1103 (all manufactured by Exxon) as polyisoprene; Beccosol EL8011, Solid Beccosol No. 31, Solid Beccosol No. 96 (all manufactured by Dainippon Ink and Chemicals, Incorporated) as an alkyd resin; and Ganex V-216, Ganex V-220 (all manufactured by Gokyo Trading Co., Ltd.) as a PVP-modified polymer can be exemplified as a commercially available product. Examples of the polymer emulsion resin include a copolymer emulsion of vinyl hydrochloride and a monomer such as ethyl acrylate, methyl methacrylate, butyl methacrylate, methacrylic acid, and vinylidene chloride. Among them, particularly, a silicone-based resin is preferable and, among other things, trimethylsiloxysilicic acid is preferable. As a commercially available product, KF7312J, and X-21-5250 (manufactured by Shin-Etsu Chemical Co., Ltd.) can be used, being not limiting.

The eyelash cosmetic of the present invention may comprise one of the (a) wax and the (b) resin or may comprise both of the (a) wax and the (b) resin. An amount of the (a) wax and/or the (b) resin in the present invention to be blended is appropriately adjusted depending on a formulation of a composition, being not particularly limiting. It is preferable that a sum of blending amounts thereof is in a range of 0.1 to 55% by mass. When a blending amount is less than 0.1% by mass, the amount is not sufficient for imparting a volume or curling effect, on the other hand, when a blending amount exceeds 55% by mass, coating is difficult, being not preferable.

It is preferable that the eyelash cosmetic of the present invention comprises both of the (a) wax and the (b) resin.

An amount of the (a) wax in the present invention to be blended is appropriately adjusted depending on a formulation of a composition, and is preferably 1 to 30% by mass, further preferably 5 to 25% by mass. When a blending amount is less than 1% by mass, the amount is not sufficient for imparting a volume or curling effect, on the other hand, when a blending amount exceeds 30% by mass, cosmetic retention is deteriorated, stickiness and hardness are increased, and coating is difficult, being not preferable.

An amount of the (b) resin in the present invention to be blended is appropriately adjusted depending on a formulation of a composition, and is preferably 0.1 to 25% by mass, further preferably 2 to 20% by mass. When a blending amount is less than 0.1% by mass, the amount is not sufficient for imparting cosmetic retention or curling effect, on the other hand, when a blending amount exceeds 25% by mass, coating becomes difficult, being not preferable.

The (c) hollow powder used in the present invention can enhance a voluminous feeling of an eyelash and, at the same time, improve a curling force and a curl retaining force. As such the (c) hollow powder, there are mainly a hollow resin powder and a hollow inorganic powder.

The hollow resin powder is such that a thermoplastic resin powder with a volatile expanding agent, which is volatilized mainly by heating, encapsulated therein has been heated, swollen or expanded.

Examples of a resin which forms a shell of this hollow expanded resin powder include a homopolymer or a copolymer composing of one or more monomers selected from a vinyl-based monomer such as vinyl chloride, vinyl acetate, and methyl vinyl ether, an acryl-based monomer such as acrylic acid, acrylic acid ester, methacrylic acid, methacrylic acid ester, acrylonitrile, and methacrylonitrile, styrene, vinylidene chloride, divinylbenzene, and ethylene glycol dimethacrylate. Preferable is a copolymer consisting of two or more kinds of monomers selected from acrylic acid, methacrylic acid or esters thereof, vinylidene chloride, acrylonitrile, and methacrylonitrile. These polymers may be crosslinked with a crosslinking agent such as divinylbenzene, ethylene glycol dimethacrylate, and triacrylformal.

The volatile expanding agent is not particularly limited, but hydrocarbon such as methane, ethane, propane, butane, isobutane, isobutene, pentane, isopentane, neopentane, hexane, neohexane, heptane, and acetylene, halogenated hydrocarbon such as trichlorofluoromethane, and dichlorodifluoromethane, and a low boiling point compound such as tetraalkylsilane are used.

This hollow resin powder is prepared by a method of heating and expanding a thermoplastic resin powder with a volatile expanding agent encapsulated therein, as disclosed, for example, in Japanese Patent Application Publication (JP-B) No. 59-53290. The hollow resin powder is generally commercially available, and examples include Matsumoto Microsphere MFL series manufactured by Matsumoto Yushi-Seiyaku Co., Ltd. [MFL-50STI (particle diameter 10 to 30 µm, true specific gravity 0.20), MFL-50 SCA (particle diameter 10 to 30 µm, true specific gravity 0.29), MFL-80 GCA (particle diameter 10 to 30 µm, true specific gravity 0.20), MFL-80 CA (particle diameter 90 to 110 µm, true specific gravity 0.13), MFL-100 SCA (particle diameter 20 to 40 µm, true specific gravity 0.20), MFL-100 CA (particle diameter 90 to 110 µm, true specific gravity 0.13), MFL-30 STI (particle diameter 10 to 30 µm, true specific gravity 0.20)], Matsumoto Microsphere F-80ED (particle diameter 90 to 110 µm, true specific gravity 0.020 to 0.030), EXPANCEL microsphere manufactured by EXPANCEL 551 DE 40 d42 (particle diameter 30 to 50 µm, true specific gravity 0.042), 551 DE 40 d60 (particle diameter 15 to 25 µm, true specific gravity 0.06), 551 DE 80 d42 (particle diameter 50 to 80 µm, true specific gravity 0.042), 461 DE 40 d60 (particle diameter 20 to 40 µm, true specific gravity 0.06), 461 DE 20 d70 (particle diameter 15 to 25 µm, true specific gravity 0.07), 051 DE 40 d60 (particle diameter 20 to 40 µm, true specific gravity 0.06), 091

DE 40 d30 (particle diameter 35 to 55 μm, true specific gravity 0.03), 091 DE 80 d30 (particle diameter 60 to 90 μm, true specific gravity 0.03), 092 DE 40 d30 (particle diameter 35 to 55 μm, true specific gravity 0.032), 092 DE 80 d30 (particle diameter 60 to 90 μm, true specific gravity 0.032), and Ganzpeal GMH-0850 manufactured by Ganz Chemical Co., Ltd. (particle diameter 8 μm, true specific gravity 0.65).

As the hollow inorganic powder, there are a powder obtained by heating, swelling or expanding an inorganic substance such as glass, which has an encapsulated volatile expanding agent which is volatilized mainly by heating, and a fly ash produced in a stage in which a coal (fine coal) is burnt. The hollow inorganic powder is generally commercially available, and examples include Scotchlite Glassbubbles K series manufactured by Sumitomo 3M [K1 (true specific gravity 0.125), K15 (true specific gravity 0.150), K20 (true specific gravity 0.200), K25 (true specific gravity 0.250), K37 (true specific gravity 0.370), K46 (true specific gravity 0.460)] and S series [S22 (true specific gravity 0.220), S38 (true specific gravity 0.380), S60 (true specific gravity 0.600)], Floated series [A16 (true specific gravity 0.16), A20 (true specific gravity 0.20), D32 (true specific gravity 0.2)], CEL STAR manufactured by Tokai Kogyo Co., Ltd. Z-20 (average particle diameter 67 μm, true specific gravity 0.17 to 0.23), Z-25 (average particle diameter 65 μm, true specific gravity 0.22 to 0.28), Z-27 (average particle diameter 63 μm, true specific gravity 0.24 to 0.30), Z-31T (average particle diameter 60 μm, true specific gravity 0.28 to 0.34), Z-36 (average particle diameter 56 μm, true specific gravity 0.33 to 0.39), SX-39 (average particle diameter 40 μm, true specific gravity 0.36 to 0.42), Z-45 (average particle diameter 52 μm, true specific gravity 0.42 to 0.48), PZ-6000 (average particle diameter 40 μm, true specific gravity 0.70 to 0.80), and Metasphere which is a fly ash balloon #50 (average particle diameter 128 μm, true specific gravity 0.6 to 0.8), #100 (average particle diameter 72 μm, true specific gravity 0.6 to 0.8).

As used herein, "true specific gravity" means a specific gravity calculated by a volume occupied by a powder particle itself and a mass thereof and, for example, when refers to "true specific gravity" of a hollow powder, it is calculated using also a space of an interior of a hollow powder particle as a volume of the particle itself. Alternatively, herein, "true specific gravity" is simply referred to as "specific gravity" hereinafter in some cases.

In addition, a surface of the (c) hollow powder may be covered with an inorganic substance. In a method of covering an inorganic powder, as disclosed, for example, in JP-A No. 4-9319, a covered powder is obtained by mixing a volatile expanding agent-encapsulated thermoplastic resin before expansion or during expansion, and an inorganic powder, and heating the mixture. Examples of other method include a method of mixing a dispersion of an inorganic power in water or an organic solvent, and a hollow resin powder, and drying this, a wet treating method of covering with a film by a method of spraying this inorganic dispersion to a hollow resin powder, and drying this, and a method of complexing by a physical force such as a high impact force.

An inorganic powder which covers a surface of the hollow resin powder is not particularly limited, but is selected depending on the desired effect, and examples include talc, sericite, mica, calcium carbonate, magnesium carbonate, kaolin, boron, nitride, titanium oxide, zinc oxide, iron oxide, cerium oxide, zirconium oxide, and silica. A particle shape of these inorganic powders is not particularly limited, and for example, may be any of a particle shape, a spherical shape, a plate shape and a needle shape, and an average particle diameter is also not particularly limited, but is preferably 0.001 to 20 μm. A mass ratio of the hollow resin powder and the inorganic powder is preferably 5:95 to 50:50.

In the present invention, the (c) hollow powder is preferably a hollow resin powder in that a voluminous feeling of an eyelash is enhanced and, at the same time, a curling force and a curl retaining force are improved and, as a resin for forming a shell, vinyl chloride, vinylidene chloride, and methyl methacrylate and the like are preferable and, as the volatile liquid expanding agent, a hydrocarbon gas is preferably used. As a commercially available product, MFL-50SCA (manufactured by Matsumoto Yushi-Seiyaku Co., Ltd.) and GMH-0850 (manufactured by Ganz Chemical Co., Ltd.) can be used, being not limiting.

An amount of the (c) hollow powder in the present invention to be blended is appropriately adjusted depending on a formulation of a composition and is preferably 0.01 to 20% by mass, further preferably 0.1 to 10% by mass. When a blending amount is less than 0.01% by mass, the amount is not sufficient for imparting a voluminous feeling, on the other hand, when a blending amount exceeds 20% by mass, usability is deteriorated, being not preferable.

In addition, in the eyelash cosmetic of the present invention, it is preferable that a ratio of a cubic volume of the (a) wax and/or the (b) resin to a cubic volume of the (c) hollow powder to be blended is 1:10 to 1:0.01. Further preferably, the ratio is 1:5 to 1:0.05. When a cubic volume of the (c) hollow powder to be blended is grater than 10-fold a total cubic volume of the (a) wax and the (b) resin, an amount of a cosmetic which can be adhered to an eyelash is decreased, a sufficient curling effect and a volume effect are not obtained, and finishing is deteriorated in some cases. On the other hand, when. a cubic volume of the (c) hollow powder is smaller than 0.01-fold a total cubic volume of the (a) wax and the (b) resin, a cosmetic itself becomes too heavy, a sufficient curling effect and curl retaining effect are not obtained, and finishing is deteriorated in some cases.

In the eyelash cosmetic of the present invention, it is preferable that, in addition to the aforementioned essential component, (d) a coloring material is further blended. Such the (d) coloring material is not particularly limited as far as it is generally used in a makeup cosmetic, and examples include inorganic pigments such as talc, mica, kaolin, calcium carbonate, zinc white, titanium dioxide, red iron oxide, yellow iron oxide, black iron oxide, ultramarine, carbon black, lower order titanium oxide, cobalt violate, chromium oxide, chromium hydroxide, cobalt titanate, bismuth oxychloride, titanium-mica pearl pigment; organic pigments such as zirconium, barium or aluminum lakes such as Red No. 201, Red No. 202, Red No. 204, Red No. 205, Red No. 220, Red No. 226, Red No. 228, Red No. 405, Orange No. 203, Yellow No. 205, Yellow No. 4, Yellow No. 5, Blue No. 1, Blue No. 404, and Green No. 3; natural pigments such as chlorophyll, and β-carotene; resin powders such as nylon, cellulose, and polyethylene; dyes. These (d) coloring materials can be used alone, or as a combination of two or more.

An amount of the (d) coloring material in the present invention to be blended is appropriately adjusted depending on a formulation of a composition, and is preferably 0.1 to 30% by mass, further preferably 3 to 20% by mass. When a blending amount is exceeding 30% by mass, a curl retaining effect is not obtained and, when the amount is less than 0.1% by mass, a cosmetic effect becomes insufficient.

In the eyelash cosmetic of the present invention, when (e) a thickener is further blended in addition to the aforementioned essential component, a viscosity can be adjusted to a suitable state, being preferable. The (e) thickener used in the present invention is not particularly limited as far as it is a compound which is usually blended as a thickener in a cosmetic, and specific examples include, as an aqueous agent, gum arabic, carrageenan, karaya gum, tragacanth gum, carob gum, quince seed (marmelo), casein, gelatin, sodium pectinate, sodium alginate, CMC, hydroxyethylcellulose, hydroxypropylcellulose, sodium polyacrylate, carboxy vinyl polymer, locust bean gum, guar gum, tamarind gum, dialkyldimethylammonium cellulose sulfate, xanthan gum, and aluminum magnesium silicate; and as an oily agent, montmorillonite group clay minerals such as bentonite, hectorite montmorillonite, beidellite, nontronite, saponite, and hectorite; organic modified clay minerals in which clay minerals such as vermiculite and bentonite are modified with a quaternary ammonium compound such as alkyltrimethylammonium chloride, dialkyldimethlyanmlonium chloride, and benzalkonium chloride; fumed silica; hydrophocized fumed silica; polysaccharide fatty acid ester such as dextrin fatty acid ester, sucrose fatty acid ester, and starch fatty acid ester; metal soap such as 12-hydroxystearic acid, calcium stearate, aluminum stearate, and aluminum myristate; high polymerization methylpolysiloxane, and crosslinked methylpolysiloxane. These (e) thickener are used by selecting one or more kinds. Among them, particularly, as an oily base, dextrin fatty acid ester, and distearyldimonium hectorite are preferable, and as an aqueous base, xanthan gum is preferable. As a commercially available product, "Rheopearl KL" and "Rheopearl KE" (both manufactured by Chiba Flour Milling Co., Ltd.) as dextrin fatty acid ester, "Benton 38 CE" (manufactured by Rheox) as distearyldimonium hectorite, and "Keltrol" and "Keltrol T" (both manufacture by CP Kelco) as xanthan gum are desirable, being not limiting.

An amount of the (e) thickener to be blended is appropriately adjusted depending on a formulation of a composition, and is preferably 0.1 to 20% by mass, further preferably 1 to 15% by mass. When a blending amount is less than 0.1% by mass, a curling effect is decreased, on the other hand, when a blending amount exceeds 20% by mass, a hardness becomes too high, and smoothness is deficient, being not preferable.

In the eyelash cosmetic of the present invention, further depending on the purpose, components which can be usually blended in a makeup cosmetic may be added in a quantitative and qualitative range that the effect of the present invention is not deteriorated. Examples of such the components include fibers, alcohols, polyhydric alcohols, drugs, surfactants, water-soluble polymers, clay minerals, antiseptics, fragrances, antioxidants, ultraviolet absorbing agents, humectants, fats or oils, and oily components such as hydrocarbon oils.

As the fiber, any fiber may be used as far as it is a fiber which is generally used in an eyelash cosmetic, and examples include 0.5 denier nylon imitation wool, 3 denier nylon imitation wool, and 11 denier nylon imitation wool. Alternatively, these fibers which are colored may be used. These fibers may be used alone, or may be used by mixing them.

In the eyelash cosmetic of the present invention, it is desirable that a specific gravity of a composition after solvent volatilization is 0.1 to 1.0. When a specific gravity is less than 0.1, preparation is practically difficult and, when a specific gravity exceeds 1.0, it is difficult to realize a curl retaining effect.

In the eyelash cosmetic of the present invention, a hardness at 30° C. (card meter; 8 mmφ/200 g load value) is preferably in a range of 70 to 180, particularly preferably in a range of 70 to 180. As used herein, a hardness is a hardness of a mascara composition before drying, and is a value measured by giving a load of 200g to a 8mmφ penetrating needle using a measuring equipment, M-301AR-type card meter (manufactured by Iiodenki) under the condition of 30° C.

The eyelash cosmetic of the present invention includes a cosmetic which is applied to an eyelash widely, such as a mascara foundation and a mascara.

The present invention will be explained further specifically below by way of Examples, but the present invention is not limited by them at all. A blending amount is indicated by % by mass.

Prior to the Examples, a method of testing and a method of evaluating the effect of the present invention will be shown.

<Hardness Measurement>

A hardness was measured by imparting a load of 200 g to a 8 mmφ penetrating needle using a measuring equipment M-301AR-type card meter (manufactured by Iiodenki) under the condition of 30° C.

<Specific Gravity of Dry Film>

A specific gravity was measured by coating each sample on a glass plate at a constant thickness (0.8 mm), drying this overnight, cutting a film part finely, and measuring a specific gravity with an AUTO TRUE DENSER MAT-5000 (manufactured by SEISHIN ENTERPRISE CO., LTD.).

<Curl-Volume Effect>

Each sample (mascara) was coated on an eyelash 10 times, and the state was evaluated with naked eyes by 20 professional panelists according to the following criteria.

(1) Evaluation of a Volume Effect

⊚: Of 20 persons, 16 or more persons answered that there is a volume effect.

○: Of 20 persons, 9 to 15 persons answered that there is a volume effect.

Δ: Of 20 persons, 5 to 8 persons answered that there is a volume effect.

×: Of 20 persons, 4 or less persons answered that there is a volume effect.

(2) Evaluation of a Curling Effect

⊚: Of 20 persons, 16 or more persons answered that there is a curling effect.

○: Of 20 persons, 9 to 15 persons answered that there is a curling effect.

Δ: Of 20 persons, 5 to 8 persons answered that there is a curling effect.

×: Of 20 persons, 4 or less persons answered that there is a curling effect.

(3) Evaluation of a Curl Retaining Effect

⊚: Of 20 persons, 16 or more persons answered that there is a curl retaining effect.

○: Of 20 persons, 9 to 15 persons answered that there is a curl retaining effect.

Δ: Of 20 persons, 5 to 8 persons answered that there is a curl retaining effect.

×: Of 20 persons, 4 or less persons answered that there is a curl retaining effect.

<Finishing>

Each sample (mascara) was coated on an eyelash and the finishing state was evaluated by 20 professional panelists according to the following criteria.

⊚: Of 20 persons, 16 or more persons answered that finishing is excellent.

○: Of 20 persons, 9 to 15 persons answered that there is finishing is excellent.

Δ: Of 20 persons, 5 to 8 persons answered that there is finishing is excellent.

×: Of 20 persons, 4 or less persons answered that there is finishing is excellent.

Blending of Hollow Powder

First, the present inventors prepared an eyelash cosmetic comprising a wax, a resin and a hollow powder, and a hardness, a specific gravity after solvent volatilization, a volume effect, a curling effect, a curl retaining effect and finishing were evaluated by the aforementioned evaluation criteria. The following Table 1 shows a blending composition of an eyelash cosmetic (mascara) used in a test, and test results.

TABLE 1

|  | Test Example | | | | |
| --- | --- | --- | --- | --- | --- |
|  | 1 | 2 | 3 | 4 | 5 |
| Light isoparaffin | To 100 | To 100 | To 100 | To 100 | To 100 |
| Decamethylcyclopentasiloxane | 20.0 | 20.0 | 20.0 | 20.0 | 20.0 |
| Microcrystalline wax | 22.0 | 17.0 | 17.0 | 17.0 | 17.0 |
| Trimethylsiloxysilicic acid | 20.0 | 15.0 | 15.0 | 15.0 | 15.0 |
| Titanium oxide | — | 5.0 | — | — | — |
| Hollow powder (MFL-50SCA, specific gravity 0.29) | — | — | 5.0 | — | — |
| (Ganzpearl GMH-0850, specific gravity 0.65) | — | — | — | 5.0 | — |
| (MFL-100 CA, specific gravity 0.20) | — | — | — | — | 5.0 |
| Black iron oxide | 5.0 | 5.0 | 5.0 | 5.0 | 5.0 |
| Dextrin fatty acid ester | 13.0 | 13.0 | 13.0 | 13.0 | 13.0 |
| Hardness | 130 | 95 | 90 | 110 | 100 |
| Specific gravity (g/cm$^3$) | 1.03 | 1.11 | 0.84 | 0.99 | 0.75 |
| Volume effect | Δ | Δ | ◉ | ◉ | ◉ |
| Curling effect | Δ | X | ◉ | ○ | ◉ |
| Curl retaining effect | Δ | X | ◉ | ◉ | ◉ |
| Finishing | X | X | ◉ | ◉ | ◉ |

(Process)

An oily phase containing a wax was heated to 90° C. to melt it, and a dispersing-treated pigment part was added thereto, and cooled to 40° C. while stirring to obtain an eyelash cosmetic (mascara).

As shown in the Table 1, in Test Example 1 in which a relatively large amount of a wax and a resin were blended, a volume effect, a curling effect, a curl retaining effect, and finishing were inferior. In addition, in Test Example 2 in which a titanium oxide powder was blended in addition to a wax and a resin, a curling effect, a curl retaining effect, and finishing were further inferior. To the contrary, in Test Examples 3 to 5 in which various hollow powders were blended together with a wax and a resin, an excellent volume effect and finishing were exhibited and, at the same time, a curling effect and a curl retaining effect were improved, demonstrating the excellent effect.

Blending Amount of Wax

Then in order to study an amount of a wax to be blended in an eyelash cosmetic, the present inventors prepared eyelash cosmetics by changing an amount of a wax to be blended variously, and evaluation was performed according to the aforementioned evaluation criteria. The following Table 2 shows a blending composition of an eyelash cosmetic (mascara) used in a test, and test results.

TABLE 2

|  | Test Example | | | | | |
| --- | --- | --- | --- | --- | --- | --- |
|  | 6 | 7 | 8 | 9 | 10 | 11 |
| Light isoparaffin | To 100 | To 100 | To 100 | To 100 | To 100 | To 100 |
| Decamethylcyclopentasiloxane | 20.0 | 20.0 | 20.0 | 20.0 | 20.0 | 20.0 |
| Microcrystalline wax | — | 3.0 | 11.0 | 24.0 | 29.0 | 35.0 |
| Liquid paraffin | 10.0 | — | — | — | — | — |
| Trimethylsiloxysilicic acid | 15.0 | 15.0 | 15.0 | 15.0 | 15.0 | 15.0 |
| Hollow powder (MFL-50SCA, specific gravity 0.29) | 4.0 | 4.0 | 4.0 | 4.0 | 4.0 | 4.0 |
| Black iron oxide | 5.0 | 5.0 | 5.0 | 5.0 | 5.0 | 5.0 |
| Dextrin fatty acid ester | 8.0 | 16.0 | 15.0 | 10.0 | 9.0 | 8.0 |
| Hardness | 90 | 100 | 90 | 100 | 95 | 90 |
| Specific gravity (g/cm$^3$) | 0.87 | 0.86 | 0.87 | 0.88 | 0.89 | 0.90 |
| Volume effect | Δ | ○ | ◉ | ◉ | ○ | ○ |
| Curling effect | ○ | ◉ | ◉ | ◉ | ◉ | ◉ |
| Curl retaining effect | ○ | ○ | ◉ | ◉ | ◉ | ◉ |
| Finishing | Δ | ○ | ◉ | ◉ | ○ | X |

As shown in the Table 2, in Test Examples 7 to 10 in which a blending amount of a wax was 3.0 to 29.0% by mass, an eyelash cosmetic excellent in all of a volume effect, a curling effect, a curl retaining effect, and finishing was obtained. On the other hand, in Test Example 6 in which liquid paraffin was blended in place of a wax, a volume effect was not obtained, and finishing was inferior. In addition, in Test Example 11 in which a wax was blended at 35.0% by mass, finishing was deteriorated.

From the foregoing results, it is preferable that an amount of a wax to be blended in the eyelash cosmetic of the present invention is around 1 to 30% by mass.

Blending Amount of Resin

Subsequently, in order to study an amount of a resin to be blended in an eyelash cosmetic, the present inventors prepared eyelash cosmetics by changing a blending amount of a resin variously, and evaluation was performed according to the aforementioned evaluation criteria. The following Table 3 shows a blending composition of an eyelash cosmetic (mascara) used in a test, and test results.

TABLE 3

| | Test Example | | | | | |
|---|---|---|---|---|---|---|
| | 12 | 13 | 14 | 15 | 16 | 17 |
| Light isoparaffin | To 100 | To 100 | To 100 | To 100 | To 100 | To 100 |
| Decamethylcyclopentasiloxane | 20.0 | 20.0 | 20.0 | 20.0 | 24.0 | 30.0 |
| Microcrystalline wax | 20.0 | 17.0 | 17.0 | 17.0 | 17.0 | 17.0 |
| Hydrogenated polybutene | 5.0 | — | — | — | — | — |
| Trimethylsiloxysilicic acid | — | 0.2 | 11.0 | 19.0 | 24.0 | 30.0 |
| Hollow powder (MFL-50SCA, specific gravity 0.29) | 4.0 | 4.0 | 4.0 | 4.0 | 4.0 | 4.0 |
| Black iron oxide | 5.0 | 5.0 | 5.0 | 5.0 | 5.0 | 5.0 |
| Dextrin fatty acid ester | 8.0 | 16.0 | 15.0 | 10.0 | 9.0 | 8.0 |
| Hardness | 90 | 100 | 90 | 100 | 95 | 80 |
| Specific gravity (g/cm³) | 0.87 | 0.86 | 0.87 | 0.88 | 0.89 | 0.87 |
| Volume effect | ○ | ⊚ | ⊚ | ⊚ | ⊚ | ○ |
| Curling effect | ○ | ⊚ | ⊚ | ⊚ | ○ | ○ |
| Curl retaining effect | Δ | ○ | ⊚ | ⊚ | ⊚ | ⊚ |
| Finishing | ○ | ○ | ⊚ | ⊚ | ○ | X |

As shown in the Table 3, in Test Examples 13 to 16 in which a blending amount of a resin was 0.2 to 30.0% by mass, an eyelash cosmetic excellent in all of a volume effect, a curling effect, a curl retaining effect, and finishing was obtained. On the other hand, in Test Example 12 in which hydrogenated polybutene was blended in place of a resin, a curl retaining effect was not obtained. In addition, in Test Example 17 in which a resin was blended at 30.0% by mass, finishing was deteriorated.

From the foregoing results, it is preferable that an amount of a resin to be blended in the eyelash cosmetic of the present invention is around 0.1 to 25% by mass.

Blending Amount of Hollow Powder

Subsequently, in order to study an amount of a hollow powder to be blended in an eyelash cosmetic, the present inventors prepared eyelash cosmetics by changing a blending amount of a hollow powder variously, and evaluation was performed according to the aforementioned evaluation criteria. The following Table 4 shows a blending composition of an eyelash cosmetic (mascara) used in a test, and test results.

TABLE 4

| | Test Example | | | | |
|---|---|---|---|---|---|
| | 18 | 19 | 20 | 21 | 22 |
| Light isoparaffin | To 100 | To 100 | To 100 | To 100 | To 100 |
| Decamethylcyclopentasiloxane | 20.0 | 20.0 | 20.0 | 20.0 | 20.0 |
| Microcrystalline wax | 3.0 | 17.0 | 17.0 | 17.0 | 17.0 |
| Trimethylsiloxysilicic acid | 3.0 | 15.0 | 15.0 | 15.0 | 15.0 |
| Hollow powder (MFL-50SCA, specific gravity 0.29) | 0.1 | 2.0 | 9.0 | 14.0 | 22.0 |
| Black iron oxide | 5.0 | 5.0 | 5.0 | 5.0 | 5.0 |
| Dextrin fatty acid ester | 13.0 | 16.0 | 15.0 | 10.0 | 9.0 |
| Hardness | 70 | 100 | 90 | 100 | 90 |
| Specific gravity (g/cm³) | 1.17 | 0.95 | 0.75 | 0.65 | 0.59 |
| Volume effect | ○ | ⊚ | ⊚ | ⊚ | X |
| Curling effect | ○ | ⊚ | ⊚ | ⊚ | Δ |
| Curl retaining effect | ⊚ | ⊚ | ⊚ | ⊚ | Δ |
| Finishing | ○ | ⊚ | ⊚ | ○ | Δ |

As shown in the Table 4, in Test Examples 18 to 21 in which a blending amount of a hollow powder was 0.1 to 14% by mass, an eyelash cosmetic excellent in all of a volume effect, a curling effect, a curl retaining effect, and finishing was obtained. On the other hand, in Test Example 22 in which a hollow powder was blended at 22.0% by mass, a volume effect, a curling effect, a curl retaining effect, and finishing were deteriorated.

From the foregoing results, it is preferable that an amount of a hollow powder to be blended in the eyelash cosmetic of the present invention is around 0.01 to 20% by mass.

Blending Amount of Coloring Material

Subsequently, in order to study an amount of a coloring material to be blended in an eyelash cosmetic, the present inventors prepared eyelash cosmetics by changing a blending amount of a coloring material variously, evaluation was performed according to the aforementioned evaluation criteria. The following Table 5 shows a blending composition of an eyelash cosmetic (mascara) used in a test and test results.

TABLE 5

| | Test Example | | | | |
|---|---|---|---|---|---|
| | 23 | 24 | 25 | 26 | 27 |
| Light isoparaffin | To 100 | To 100 | To 100 | To 100 | To 100 |
| Decamethylcyclopentasiloxane | 20.0 | 20.0 | 20.0 | 20.0 | 20.0 |
| Microcrystalline wax | 17.0 | 17.0 | 17.0 | 17.0 | 17.0 |
| Trimethylsiloxysilicic acid | 15.0 | 15.0 | 15.0 | 15.0 | 15.0 |

TABLE 5-continued

|  | Test Example | | | | |
| --- | --- | --- | --- | --- | --- |
|  | 23 | 24 | 25 | 26 | 27 |
| Hollow powder (MFL-50SCA, specific gravity 0.29) | 4.0 | 4.0 | 4.0 | 4.0 | 4.0 |
| Black iron oxide | 0.2 | 5.0 | 14.0 | 25.0 | 35.0 |
| Dextrin fatty acid ester | 15.0 | 13.0 | 10.0 | 10.0 | 10.0 |
| Hardness | 80 | 100 | 90 | 130 | 110 |
| Specific gravity (g/cm³) | 0.82 | 0.88 | 0.99 | 1.13 | 1.25 |
| Volume effect | ○ | ◎ | ◎ | ◎ | ○ |
| Curling effect | ◎ | ◎ | ◎ | ○ | Δ |
| Curl retaining effect | ◎ | ◎ | ◎ | ○ | X |
| Finishing | ○ | ◎ | ◎ | ○ | X |

As shown in Table 5, in Test Examples 23 to 26 in which a blending amount of a coloring material was 0.2 to 25.0% by mass, an eyelash cosmetic excellent in all of a volume effect, a curling effect, a curl retaining effect, and finishing was obtained. On the other hand in Test Example 27 in which a coloring material was blended at 35.0% by mass, a curl retaining effect was inferior, and finishing was deteriorated.

From the foregoing results, it is preferable that an amount of a coloring material to be blended in the eyelash cosmetic of the present invention is around 0.1 to 30% by mass.

Cubic Volume Ratio of a Wax and a Resin, to a Hollow Powder

In addition, the present inventors further studied a preferable blending amount of various components in detail and, for example, it was seen that although the same amount of a hollow powder is blended, the effect is different depending on a kind of a hollow powder to be blended, in some cases. And from this, the present inventors thought that the effect of the present invention do not simply depend on a blending amount of various components, paid an attention to a ratio of a cubic volume of a wax and a resin, and a cubic volume of a hollow powder to be blended, and studied a relationship with the effect.

In order to study a preferable cubic volume ratio of a wax and a resin, to a hollow powder in an eyelash cosmetic, the present inventors prepared eyelash cosmetics in which a cubic volume ratio of a wax and a resin, to a hollow powder was variously changed, by appropriately adjusting blending amounts of a wax, a resin, and a hollow powder, and evaluation was performed according to the aforementioned evaluation criteria. As a hollow powder, two kinds of hollow powders having a specific gravity of 0.20 and 0.03, respectively, were used to perform the similar test. In addition, regarding a wax and a resin, calculation was performed using a specific gravity of 1.0. The following Tables 6 and 7 show a blending composition of an eyelash cosmetic (mascara) used in a test and test results.

TABLE 6

|  | Test Example | | | | | | | |
| --- | --- | --- | --- | --- | --- | --- | --- | --- |
|  | 28 | 29 | 30 | 31 | 32 | 33 | 34 | 35 |
| Light isoparaffin | To 100 | To 100 | To 100 | To 100 | To 100 | To 100 | To 100 | To 100 |
| Decamethylcyclopentasiloxane | 20.0 | 20.0 | 20.0 | 20.0 | 20.0 | 20.0 | 20.0 | 20.0 |
| Microcrystalline wax | 2.0 | 3.0 | 10.0 | 30.0 | 2.0 | 10.0 | 10.0 | 30.0 |
| Polyethylene wax | — | — | 10.0 | 10.0 | — | 5.0 | 5.0 | 10.0 |
| Trimethylsiloxysilicic acid | 0.5 | 2.0 | 5.0 | 10.0 | 0.5 | 5.0 | 10.0 | 10.0 |
| Hollow powder (MFL-100SCA, specific gravity 0.20) | 10.0 | 10.0 | 5.0 | 2.0 | 0.1 | 0.2 | 0.05 | 0.05 |
| Black iron oxide | 5.0 | 5.0 | 5.0 | 5.0 | 1.0 | 5.0 | 2.0 | 5.0 |
| Dextrin fatty acid ester | 10.0 | 5.0 | 5.0 | 5.0 | 20.0 | 10.0 | 10.0 | 5.0 |
| Cubic volume of wax + resin (cm³) | 2.5 | 5.0 | 25.0 | 50.0 | 2.5 | 20.0 | 25.0 | 50.0 |
| Cubic volume of hollow powder (cm³) | 50.0 | 50.0 | 25.0 | 10.0 | 0.5 | 1.0 | 0.25 | 0.25 |
| Wax + resin:hollow powder (cubic volume ratio) | 1:20 | 1:10 | 1:1 | 1:0.2 | 1:0.2 | 1:0.05 | 1:0.01 | 1:0.005 |
| Hardness | 50 | 90 | 100 | 120 | 130 | 50 | 100 | 120 |
| Specific gravity (g/cm³) | 0.43 | 0.41 | 0.69 | 0.88 | 1.00 | 1.00 | 0.99 | 1.18 |
| Volume effect | Δ | ◎ | ◎ | ◎ | ○ | ○ | ○ | ○ |
| Curling effect | Δ | ○ | ◎ | ◎ | ◎ | ◎ | ◎ | Δ |
| Curl retaining effect | Δ | ○ | ◎ | ◎ | ◎ | ◎ | ◎ | Δ |
| Finishing | Δ | ○ | ◎ | ◎ | ○ | ○ | ○ | X |

TABLE 7

|  | Test Example | | | | | | | |
| --- | --- | --- | --- | --- | --- | --- | --- | --- |
|  | 36 | 37 | 38 | 39 | 40 | 41 | 42 | 43 |
| Light isoparaffin | To 100 | To 100 | To 100 | To 100 | To 100 | To 100 | To 100 | To 100 |
| Decamethylcyclopentasiloxane | 20.0 | 20.0 | 20.0 | 20.0 | 20.0 | 20.0 | 20.0 | 20.0 |
| Microcrystalline wax | 2.0 | 3.0 | 10.0 | 30.0 | 2.0 | 10.0 | 20.0 | 30.0 |
| Polyethylene wax | — | — | 10.0 | 10.0 | — | 5.0 | 10.0 | 10.0 |
| Trimethylsiloxysilicic acid | 0.5 | 2.0 | 5.0 | 10.0 | 0.5 | 5.0 | 10.0 | 10.0 |
| Hollow powder (091DE40d30: specific gravity 0.03) | 1.5 | 1.5 | 0.75 | 0.3 | 0.015 | 0.03 | 0.012 | 0.0075 |
| Black iron oxide | 5.0 | 5.0 | 5.0 | 5.0 | 1.0 | 5.0 | 5.0 | 5.0 |
| Dextrin fatty acid ester | 10.0 | 5.0 | 5.0 | 5.0 | 20.0 | 10.0 | 5.0 | 5.0 |
| Cubic volume of wax + resin (cm³) | 2.5 | 5.0 | 25.0 | 50.0 | 2.5 | 20.0 | 40.0 | 50.0 |
| Cubic volume of hollow powder (cm³) | 50.0 | 50.0 | 25.0 | 10.0 | 0.5 | 1.0 | 0.4 | 0.25 |
| Wax + resin:hollow powder (cubic volume ratio) | 1:20 | 1:10 | 1:1 | 1:0.2 | 1:0.2 | 1:0.05 | 1:0.01 | 1:0.005 |
| Hardness | 60 | 70 | 80 | 100 | 130 | 100 | 60 | 100 |

TABLE 7-continued

| | Test Example | | | | | | | |
|---|---|---|---|---|---|---|---|---|
| | 36 | 37 | 38 | 39 | 40 | 41 | 42 | 43 |
| Specific gravity (g/cm³) | 0.30 | 0.27 | 0.61 | 0.86 | 1.00 | 1.00 | 1.00 | 0.99 |
| Volume effect | Δ | ◎ | ◎ | ◎ | ○ | ◎ | ○ | Δ |
| Curling effect | Δ | ○ | ◎ | ◎ | ◎ | ◎ | ◎ | Δ |
| Curl retaining effect | Δ | ○ | ◎ | ◎ | ◎ | ◎ | ○ | X |
| Finishing | Δ | ○ | ◎ | ◎ | ◎ | ○ | ○ | X |

As shown in Table 6, when a hollow powder having a specific gravity of 0.2 is used, in Test Examples 29 to 34 in which a ratio of a total cubic volume of a wax and a resin, and a cubic volume of a hollow powder was adjusted to be 1:10 to 1:0.01, volume, and finishing are excellent and, at the same time, a curling effect, and a curl retaining effect are improved, and an eyelash cosmetic excellent in various effects was obtained. On the other hand, in Test Example 28 in which the cubic volume ratio was adjusted to be 1:20, since amounts of a wax and a resin were relatively small, and an amount of adhesion to an eyelash is decreased, a curling effect, and a volume effect were not obtained and, further, finishing was also deteriorated. In addition, in Test Example 35 in which the cubic volume ratio was adjusted to be 1:0.005, since an amount of a hollow powder was relatively small, and a mascara itself was too heavy, a curling effect, and a curl retaining effect are not satisfactory and, further, finishing was also deteriorated.

Further, as shown in the Table 7, also when a hollow powder having a specific gravity of 0.03 is used, it was seen that, in Test Examples 37 to 42 in which a ratio of a total cubic volume of a wax and a resin, and a cubic volume of a hollow powder is 1:10 to 1:0.01, an eyelash cosmetic excellent in various effects is obtained, like the results of Table 6.

From the foregoing results, it is thought that the effect of blending a wax, a resin and a hollow powder in the eyelash cosmetic of the present invention is associated with a cubic volume ratio of various components rather than a blending amount of various components, and it is preferable that the ratio of a cubic total volume of a wax and a resin, and a cubic volume of a hollow powder is in a range of 1:10 to 1:0.01.

EXAMPLE 1

Emulsified Film-Type Mascara

| A: Bentonite | 2.0% |
|---|---|
| Sodium carboxymethylcellulose (low viscosity) | 0.2% |
| Purified water | 10.0% |
| B: Sodium lauryl sulfate | 0.1% |
| Butylene glycol | 1.5% |
| Purified water | remainder |
| C: Beeswax | 6.5% |
| Liquid paraffin | 3.5% |
| Carbon black | 1.5% |
| D: Stearic acid | 1.0% |
| Carnauba wax | 5.0% |
| E: Morpholine | 0.4% |
| F: Vinyl acetate emulsion | 30.0% |
| H: Hollow powder (GMH-0850) | 2.0% |
| Antiseptic | quantum sufficit |

(Process)
(1) Bentonite and sodium carboxymethylcellulose were mixed in the dry state, and the mixture was added to heated purified water to swell it to be uniform (A).
(2) To this was added B, and this was heated to 65 to 70° C.
(3) D was added to C, this was heated to melt it, cooled, kneaded with a heat roll mill, re-melted, and heated to 70° C.
(4) E was added to a mixture of A and B, a mixture of C and D was further added thereto, this was emulsified, and cooled while stirring.

EXAMPLE 2

Oily Emulsified-Type Mascara

| Carnauba wax | 7.0% |
|---|---|
| Beeswax | 2.0% |
| Microcrystalline wax | 20.0% |
| Lanolin | 0.4% |
| Liquid polyisobutylene | remainder |
| Polyvinyl pyrrolidone | 1.0% |
| Organic modified bentonite | 3.0% |
| Black iron oxide | 10% |
| Hollow powder (MFL-50SCA) | 10.0% |
| Antiseptic | quantum sufficit |

(Process)
Organic modified bentonite was added to a part of liquid polyisobutylene, and this was dispersed through a colloid mill, and gelled. Then, waxes and an antiseptic were mixed, the mixture was heated to melt it, a pigment was added, this was cooled, kneaded with a role mill, heated again to melt it, the bentonite gel and a remaining liquid polyisobutylene were added, and this was cooled while stirring.

EXAMPLE 3

Oil-In-Water Mascara

| (Oily phase) | |
|---|---|
| Light isoparaffin (Isopar E) | remainder |
| Organic modified clay mineral | 3.0% |
| Polyisoprene resin | 10.0% |
| Hollow powder (GMH-0850) | 2.0% |
| Carnauba wax | 0.1% |
| Fragrance | quantum sufficit |
| (Aqueous phase) | |
| Water | 41.0% |
| Water-swelling clay mineral | 3.0% |
| Propylene glycol | 5.0% |
| Carbon black | 10.0% |
| Antiseptic | quantum sufficit |
| POE (15) oleyl ether | 1.0% |

(Process)

Oily phase: A part of light isoparaffin was heated to 90° C., a polyisoprene resin was dissolved and, thereafter, a remaining light isoparaffin resin and other oil phase components were mixed, and the mixture was cooled as it was while stirring.

Aqueous phase: A water-swelling clay mineral was placed into a part of water, this was sufficiently swollen with a homomixer, remaining aqueous phase components were placed therein, and the mixture was stirred.

Then, to the above-prepared aqueous phase was gradually added the oily phase while stirring at room temperature, thereby, the material was emulsified, and sufficiently emulsified with a homomixer or a disperser to prepare the mascara.

EXAMPLE 4

Water-In-Oil Mascara

| (Oily phase) | |
|---|---|
| Light isoparaffin | 7.0% |
| Methylpolysiloxane | 2.0% |
| Decamethylcyclopentasiloxane | 10.0% |
| Microcrystalline wax | 0.1% |
| Trimethylsiloxysilicic acid | 10.0% |
| Methylpolysiloxane emulsion | quantum sufficit |
| Polyethylene glycol dioleate | 2.0% |
| Diglyceryl diisostearate | 2.0% |
| DL-α-tocopherol acetate | 0.1% |
| Dimethyldistearylammonium hectorite | 6.0% |
| Hollow powder (MFL-50SCA) | 2.0% |
| (Aqueous phase) | |
| 1,3-Butylene glycol | 4.0% |
| Sodium bicarbonate | 0.2% |
| Paraoxybenzoic acid ester | quantum sufficit |
| Sodium dehydroacetate | quantum sufficit |
| Black iron oxide | 7.0% |
| Seaweed extract | 0.1% |
| Bentonite | 1.0% |
| Polyvinyl acetate emulsion | 30.0% |
| Purified water | remainder |

(Process)

An aqueous phase is added to an oily phase heated at 80° C. while stirring, and this is emulsified with a disperser. After emulsification, the emulsion is stirred and cooled to remove it.

EXAMPLE 5

Oil-In-Water Mascara

| (Aqueous phase) | |
|---|---|
| Purified water | remainder |
| 1,3-Butylene glycol | 7.0% |
| Polyethyl acrylate | 10.0% |
| Polyvinyl acetate | 5.0% |
| Polyvinyl alcohol | 1.0% |
| Isopropanol | 2.0% |
| Xanthan gum | 0.1% |
| Seaweed extract | 0.1% |
| Caustic potash | 0.4% |
| Palmitic acid | 1.3% |
| Cellulose gum | 0.2% |
| Paraben | quantum sufficit |
| Phenoxy ethanol | quantum sufficit |
| Black iron oxide | 10.0% |
| (Oily phase) | |
| Cyclomethicone | 15.0% |
| Trimethylsiloxysilicic acid | 15.0% |
| Jojoba ester | 3.0% |
| Glyceryl stearate | 1.2% |
| Stearic acid | 2.1% |
| Phenyltrimethicone | 0.4% |
| Di(phytosteryl/octyldodecyl) lauroylglutamate | 0.1% |
| Bentonite | 1.0% |
| Tocopherol acetate | 0.1% |
| Batyl alcohol | 0.7% |
| Hollow powder (GMH-0850) | 1.0% |
| Fragrance | quantum sufficit |

(Process)

An aqueous phase part and an oil phase part heated to 80° C. are added while stirring, and this is emulsified with a homomixer. After emulsification, the emulsion is stirred and cooled to remove it.

EXAMPLE 6

Oil-In-Water Mascara

| | | |
|---|---|---|
| (1) | Stearic acid | 3.0% |
| (2) | Cetyl-α-monoglycerin ether | 1.0% |
| (3) | Sucrose oleic acid ester (substitution degree 1.2, monoester content 40% by mass) | 3.0% |
| (4) | Beeswax | 15.0% |
| (5) | Polyacrylic acid ester emulsion (solid part) | 8.0% |
| (6) | POE (20) sorbitan monostearate | 1.0% |
| (7) | Isopropanol | 2.0% |
| (8) | Bentonite | 0.5% |
| (9) | Black iron oxide | 8.0% |
| (10) | Hollow powder (GMH-0850) | 2.0% |
| (11) | Ethyl paraben | quantum sufficit |
| (12) | Ion-exchanged water | remainder |
| (13) | Sodium hydroxide | 0.3% |
| (14) | Fragrance | quantum sufficit |

(Process)

(1), (2) and (4) were heated to 90° C. to melt, this was added to a dispersion obtained by heating (3), (6), and (8) to (13) to 85° C., this was dispersed with a homomixer, (5), (7) and (14) were further added, and the mixture was cooled to 40° C. while stirring to obtain an eyelash cosmetic (mascara).

(Evaluation)

This was evaluated for a voluminous feeling, easiness of overlaying, finishing, and usability according to the aforementioned evaluation criteria, and the result was voluminous felling: ○, easiness of overlaying: ⊚, finishing: ⊚, and usability: ⊚

As described in detail, according to the present invention, an eyelash cosmetic which has realized a voluminous feeling, and a curling effect and a curl retaining effect at the same time can be provided.

What is claimed is:

1. A method of curling eyelashes comprising applying to eyelashes with a brush an eyelash cosmetic comprising at least one of (a) a wax and a (b) a resin, together with (c) a hollow resin powder, wherein the eyelash cosmetic exhibits a hardness at 30° C. (card meter; 8 mmφ/200 g load value) in a range of 70 to 180.

2. The method of claim 1, wherein the eyelash cosmetic comprises: 0.1 to 55% by mass of at least one of (a) the wax and (b) the resin, and 0.01 to 20% by mass of (c) the hollow resin powder.

3. The method of claim 1, wherein the eyelash cosmetic comprises: 1 to 30% by mass of (a) the wax, 0.1 to 25% by mass of (b) the resin, and 0.01 to 20% by mass of (c) the hollow resin powder.

4. The method of claim 1, wherein the resin powder has an average particle diameter of 8 microns or greater.

5. The method of claim 1, wherein the true specific gravity of the hollow resin powder is 0.02 to 0.65.

6. The method of claim 1, wherein the eyelash cosmetic comprises: 5 to 25% by mass of (a) a wax, 2 to 20% by mass of (b) a resin, and 0.1 to 10% by mass of (c) a hollow resin powder.

7. The method of claim 1, wherein the ratio of the combined volume of (a) the wax and (b) the resin to the volume of (c) the hollow resin powder, said ratio represented by (a+b)÷c, is 1:10 to 1:0.01.

8. The method of claim 2, wherein the ratio of the combined volume of (a) the wax and (b) the resin to the volume of (c) the hollow resin powder, said ratio represented by (a+b)÷c, is 1:10 to 1:0.01.

9. The method of claim 1, wherein the ratio of the combined volume of (a) the wax and (b) the resin to the volume of (c) the hollow resin powder, said ratio represented by (a+b)÷c, is 1:5 to 1:0.05.

10. The method of claim 1, wherein the eyelash cosmetic further comprises: 0.1 to 30% by mass of (d) a coloring material.

11. The method of claim 2, wherein the eyelash cosmetic further comprises: 0.1 to 30% by mass of (d) a coloring material.

12. The method of claim 1, wherein the eyelash cosmetic further comprises: 0.1 to 20% by mass of (e) a thickener.

13. The method of claim 1, wherein the eyelash cosmetic further comprises a solvent, and wherein the eyelash cosmetic has a specific gravity after solvent volatilization of 0.1 to 1.0.

14. The method of claim 1, wherein the eyelash cosmetic further comprises (d) a hollow glass powder.

15. The method of claim 1, wherein the eyelash cosmetic further comprises (d) a hollow inorganic powder.

16. The method of claim 1, wherein the eyelash cosmetic further comprises a film of an inorganic powder at least partially covering the resin powder.

17. The method of claim 1, wherein the hollow resin powder (c) has an average particle diameter of 10 microns or greater.

18. The method of claim 1, wherein the eyelash cosmetic comprises: 1 to 30% by mass of (a) a wax, 0.1 to 25% by mass of (b) a resin, and 0.01 to 20% by mass of (c) a hollow resin powder, wherein the true specific gravity of the hollow resin powder is 0.02 to 0.65, and (d) 0.01 to 20% by mass of a hollow inorganic powder.

19. The method of claim 1, wherein the eyelash cosmetic comprises 11 to 19% by mass of the resin.

20. The method of claim 1, wherein the eyelash cosmetic comprises 11 to 24% by mass of the wax.

* * * * *